United States Patent [19]

Cox

[11] 4,000,200
[45] Dec. 28, 1976

[54] PREPARATION OF KETONES FROM OLEFINS

[75] Inventor: James K. Cox, Houston, Tex.

[73] Assignee: Petro-Tex Chemical Corporation, Houston, Tex.

[22] Filed: Feb. 8, 1971

[21] Appl. No.: 113,739

[52] U.S. Cl. .................. 260/597 R; 260/586 P; 260/590 R; 260/592; 260/621 C; 260/590 B; 260/638 R; 260/590 FA; 260/526 R
[51] Int. Cl.$^2$ ................................... C07C 45/04
[58] Field of Search .......... 260/597 R, 586 B, 592, 260/635 H

[56] References Cited

UNITED STATES PATENTS

| | | | |
|---|---|---|---|
| 2,726,255 | 12/1955 | Walker et al. | 260/597 R X |
| 3,102,147 | 8/1963 | Johnson | 260/597 R X |

Primary Examiner—James O. Thomas, Jr.
Assistant Examiner—James H. Reamer
Attorney, Agent, or Firm—N. Elton Dry; Kenneth H. Johnson

[57] ABSTRACT

Olefins oxidized with organic hydroperoxides in the presence of water and the appropriate metal catalyst at temperatures in the range of 140° to 250° C. give high yields of the corresponding ketone (based on the hydroperoxide charged.) For example, 2-methyl-2-butene reacted at 155° C. at autogenous pressure in the presence of $H_2O$ and molybdenum ions with 1.008 moles of t-butylhydroperoxide gave 0.90 mole of 2-methyl-3-butanone, a 90% yield.

16 Claims, No Drawings

PREPARATION OF KETONES FROM OLEFINS

This invention relates to the preparation of ketones. More particularly it relates to a process for the preparation of ketones from olefins.

Briefly stated, the present invention is a process for preparing ketones which comprises reacting an olefinically unsaturated compound with an organic hydroperoxide in the presence of water and a catalytic amount of a compound of a metal selected from the group consisting of molybdenum, vanadium, tungsten, titanium, niobium, tantalum, rhenium, selenium, chromium, zirconium, tellurium and uranium at a temperature in the range of 140° to 250° C.

The olefinic compounds which are employed as starting materials in the present process include substituted and unsubstituted acyclic and cyclic mono olefins. Substituents are those which will be inert in the reaction, such as halogens, e.g., bromine, chlorine, iodine and fluorine, carboxy groups, hydroxyl groups, oxo alkoxy groups, hydrocarbon groups such as alkyl, cycloalkyl and aryl, aralkyl, alkaryl and the like. The olefinic compound will normally comprise 4 to 30 carbon atoms in a structure as

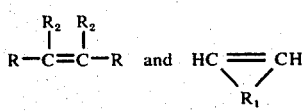

where each R is independently selected from organic radicals containing from 1 to 14 carbon atoms, $R_1$ is an organic radical having 2 to 28 carbon atoms and each $R_2$ is independently selected from hydrogen or organic radicals containing 1 to 14 carbon atoms.

In the oxidation of the olefinic substrate, the ratio of substrate to organic peroxy compounds can vary over a wide range. Generally, mole ratios of olefinic compounds to hydroperoxide in the range of 0.5:1 to 100:1 preferably 1:1 to 20:1 and more preferably 2:1 to 10:1 are employed.

Some representative olefinic compounds are 2-butene, 2-methyl-2-butene, 2-pentene, 3-methyl-2-pentene, 4-ethyl-2-pentene, 2-hexene, 3-hexene, 2,5-dimethyl-3-hexene, 2-octene, 8,9-dimethyl-2-decene, eicosene, triacontene, cyclopentene, cyclohexene, 3-methyl-cyclohexene, cycloheptene, cycloheptadecene, cyclotricontene, 3-chlorocyclopentene, 3-bromocyclohexene, 1-phenyl cyclohexene, 3-cyclohexene-1-carboxaldehyde, 3-cyclohexene-1-carboxylic acid, 2-cyclohexene-1-ol, ethyl-3-cyclohexene-1-carboxylate, 4-chloro-2-heptene, 2-hepten-4-ol, 2-chloro-2-octene, 1,4-dibromo-2-butene, 1,4-dichloro-2-methyl-2-butene, 2-butene-1,4 diol, 2-butenoic acid, β-methyl styrene, 1-chloro-1phenyl propene, bicyclo[3.1.0] hex-2-ene, spiro[2.5] oct-5-ene, spiro[bicyclo[2.1.0] pent-2-ene-5,1'-cyclopentane] and the like.

This process is particularly useful for lower olefins having 4 to 6 carbon atoms and in particular the hydrocarbons. The process follows the sequence as illustrated by: 2-butene to methyl ethyl ketone, 2-pentene to methyl propyl ketone and diethyl ketone, 2-methyl-2-butene to methyl isopropyl ketone, 3-hexene to ethyl propyl ketone, cyclohexene to cyclohexanone and so forth.

The reaction is carried out using an organic hydroperoxide reactant having the structure ROOH where R is an organic radical, usually a substituted or unsubstituted alkyl, cycloalkyl, aralkyl, alkaryl, aralkenyl, hydroxyaralkyl, cycloalkenyl, hydroxycycloalkyl or the like having about 3 to 20 carbon atoms.

The concentration of hydroperoxides in the substrate oxidation reaction mixture at the beginning of the reaction will normally be 1 percent or more although lesser concentrations will be effective and can be used.

Some suitable hydroperoxides are tertiary butyl hydroperoxide, isoamyl hydroperoxide, t-amyl hydroperoxide, methyl ethyl ketone hydroperoxide, cyclohexanone hydroperoxide, methylcyclohexene hydroperoxide, cumene hydroperoxide, ethyl benzene hydroperoxide, toluene hydroperoxide, ethyl toluene hydroperoxide, o-xylene hydroperoxide, phenylcyclohexane hydroperoxide and the like.

The hydroperoxides employed in this invention can be prepared by oxidation of the corresponding hydrocarbon. The oxidation is generally carried out using molecular oxygen as provided by, e.g., air. Broadly oxidation temperatures are in the range of 40° to 180° C. or preferably about 90° to 140° C. with pressures of 1 to 70 atmospheres preferably around 2 to 30 atmospheres. Suitable procedures for producing hydroperoxides are shown in U.S. Pat. Nos. 2,831,023, 3,096,376 and 3,510,526. Further descriptions on the preparation of organic peroxides can be found in "Organic Peroxides, Their Formation and Reactions", E. G. E. Hawkins, D. Van Nostrand Company, Inc., Princeton, N.J., 1961 and "Organic Peroxides", A. G. Davies, Butterworths, London, 1961, which are incorporated herein by reference.

It is a beneficial result of this invention that the reaction of the hydroperoxide with the olefinic compound converts the hydroperoxide almost quantitatively to the corresponding alcohol. This alcohol can be recovered as a product, per se or can be reconverted to the olefin, hydrogenated, then autoxidized to the hydroperoxide.

In one embodiment of the invention the hydroperoxide serves also as a source of olefinic feed for the reaction, e.g.

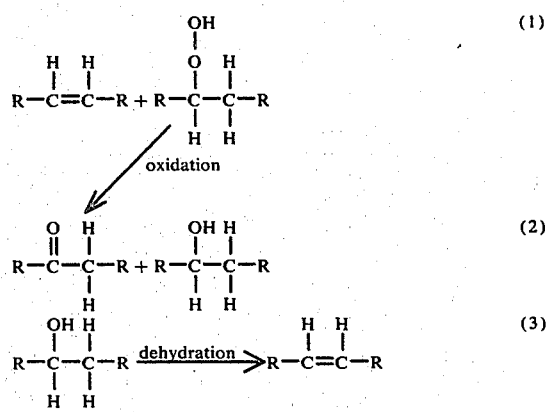

where R is as previously defined.

The catalyst employed in this reaction are the compounds of Mo, V, W, Ti, Nb, Ta, Re, Se, Cr, Zr, Te, U or mixtures of such compounds. Although the reaction proceeds in both a homogenous and heterogenous catalyst system, a homogenous system is preferred. Thus in the preferred system a soluble compound of the catalyst metal is employed.

The amount of metal in solution used as catalyst in the reaction can be varied widely, although as a rule it is desirable to use at least 0.00001 mole and preferably 0.001 to 0.03 mole per mole of hydroperoxide present. Amounts as low as 0.000001 mole per mole of hydroperoxide have an effect while amount greater than about 0.1 mole seem to give no advantage over smaller amounts, although amounts up to 1 mole or more per mole of hydroperoxide can be employed. The catalysts remain dissolved in the reaction mixture throughout the process and can be reused in the reaction after removal of the reaction products therefrom. The metal compounds include the organic salts, the oxides such as $Mo_2O_3$, $MoO_2$, acids, the chlorides and oxychlorides, fluorides, phosphates, sulfides, and the like. Heteropolyacids containing the metal can be used as can salts thereof; examples include phosphomolybdic acid and the sodium and potassium salts thereof.

The catalysts are suitably added as soluble compounds. It is possible, however, to add the catalyst as finely divided metal with the metal being eventually converted to a compound sufficiently soluble to provide a catalytic amount of the metal in solution in the reaction mixture.

The catalytic components may be employed in the reaction in the form of a compound or mixture which is initially soluble in the reaction medium. While solubility will, to some extent depend on the particular reaction medium employed, a suitably soluble substance contemplated by the invention would include hydrocarbon soluble, organo-metallic compounds having a solubility in methanol at room temperature of at least 0.1 gram per liter. Illustrative soluble forms of the catalytic materials are the naphthenates, sterates, octoates, carbonyls and the like. Various chelates, association compounds and enol salts, such as, for example, acetoacetonates may also be used. Specific and preferred catalytic compounds of this type for use in the invention are the naphthenates and carbonyls of molybdenum, vanadium, titanium, tungsten, rhenium, columbium, tantalum, osmium, selenium, chromium, zirconium, tellurium and uranium. Alkoxy compounds such as tetrabutyl titanate and like tetra alkyl titanates are very useful.

Other exemplary compounds are molybdenum (III) oxide, molybdenum (IV) oxide, molybdic acid, molybdenum pentachloride, molybdenum dichloride, molybdenum dioxydichloride, vanadium tribromide, vanadium dichloride, titanium dichloride, tungsten hexachloride, tungsten tetraiodide, rhenium trichloride, columbium monoxide, columbium oxychloride, tantalum bromide, osmium tetraoxide, selenium dioxide, selenium oxyfluoride, chromium (II) bromide, chromium (III) nitrate, chromium trioxide, hexaureachromium (III) perrhenate, zirconium tetrachloride, zirconium nitrate, zirconium selenate, zirconyl iodide, tellurium tetrachloride, uranium tetrachloride, uranyl acetate, uranyl bromide, uranyl nitrate and so forth.

Molybdenum, tungsten, vanadium and titanium form a preferred group which is particularly useful for oxidizing the previously described lower olefins as well as the other described olefinic materials.

An essential feature of the present invention is the presence of water in the reaction. Water is usually present in a range of about 0.5 to 10 moles per mole of hydroperoxide, preferably about 1 to 60 moles per mole. The best results were obtained at about 2.5 to 4.5 moles of water per mole of hydroperoxide.

The reaction is carried out at a temperature in the range of 140° to 250° C., preferably about up to 180° C. The temperature of reaction is an important feature of the invention since very poor results are achieved at temperatures below 140° C.

The reaction is carried out at pressure conditions sufficient to maintain a liquid phase. Although subatmoshperic pressures can be employed, pressures usually in the range of about atmospheric to about 1,000 p.s.i.g. are most desirable.

In addition to the water which is present in the reaction organic solvents can be used. Among the suitable substances are hydrocarbons, which may be aliphatic, naphthenic or aromatic, and the oxygenated derivatives of these hydrocarbons. Preferably, the solvent has the same carbon skeleton as the hydroperoxide used, so as to minimize or avoid solvent separation problems.

It is generally advantageous to carry out the reaction to achieve as high a hydroperoxide conversion as possible, preferably at least 50% and desirably at least 90%, consistent with reasonable selectivities. Reaction times ranging from a minute to many hours, preferably about 10 minutes to 10 hours are suitable, while 20 minutes to 3 hours are usually employed.

The hydroperoxide can be added to the reaction in a single step or it can be added in increments to the reaction. The reaction can be run either batchwise or in a continuous manner with appropriate conventional equipment and techniques.

The ketones are widely used as chemcial intermediates, reactants and solvents, for example, methyl ethyl ketone.

EXAMPLE 1

A 1 liter Parr bomb containing 1.008 moles of t-butyl hydroperoxide (TBHP), 2.833 moles of 2-methyl butene-2, 4.20 moles of $H_2O$ and 2.8 grams of molybdenum naphthenate ($23.7 \times 10^{-4}$ moles of Mo) was heated to 155° C. for 2 hours. Conversion of t-butyl hydroperoxide was 100%. Based on the hydroperoxide charged the yield of methyl isopropyl ketone was 90% as determined by gas chromatography.

EXAMPLE 2

The same process carried out at 120° C. for 2 hours using 1.00 mole of t-butyl hydroperoxide, 3.08 moles of 2-methyl butene-2, 3.64 moles of $H_2O$ and 1.3 grams of molybdenum naphthenate ($10.8 \times 10^{-4}$ moles of Mo) gave only 5.7% yield of methyl isopropyl ketone based on hydroperoxide charged (97% conversion).

EXAMPLE 3

A second run at 120° C. using 2.3 grams of molybdenum naphthenate ($16.3 \times 10^{-4}$ moles of Mo), 3.08 moles 2-MB-2, 1 mole TBHP and 3.61 moles of $H_2O$ gave only 6.8% methyl isopropyl ketone based on hydroperoxide charged (96% conversion).

The invention claimed is:

1. A process for preparing ketones which comprises reacting an olefinically unsaturated hydrocarbon compound having 4 to 30 carbon atoms and a structure selected from the group consisting of

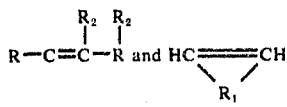 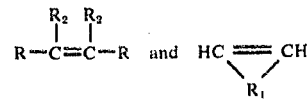

where each R is independently a hydrocarbon radical containing from 1 to 14 carbon atoms, $R_1$ is a hydrocarbon radical having 2 to 28 carbons and each $R_2$ is independently hydrogen or a hydrocarbon radical containing 1 to 14 carbon atoms, with an organic hydroperoxide having the structural formula $R_3OOH$ wherein $R_3$ is an alkyl, cycloalkyl, aralkyl, alkaryl, aralkenyl, hydroxyaralkyl, cycloalkenyl, or hydroxycycloalkyl hydrocarbon radical having 3 to 20 carbon atoms in the presence of water and a catalytic amount of an organo-metallic compound of a metal selected from the group consisting of molybdenum, vanadium, tungsten, titanium, niobium, tantalum, rhenium, selenium, chromium, zirconium, tellurium and uranium, said compound being hydrocarbon soluble and having a solubility in methanol at room temperature of at least 0.1 gram per liter at a temperature in the range of 140° to 250° C.

2. The process according to claim 1 wherein the mole ratio of olefinically unsaturated compound to organic hydroperoxide is in the range of 0.5:1 to 100:1.

3. The process according to claim 2 wherein the olefinically unsaturated hydrocarbon compound has 4 to 6 carbon atoms.

4. The process according to claim 2 wherein there is from 0.00001 to 0.1 mole of catalyst per mole of organic hydroperoxide.

5. The process according to claim 4 wherein the metal comprises molybdenum, tungsten, vanadium or titanium.

6. The process according to claim 4 wherein there is from 0.001 to 0.03 mole of catalyst per mole of organic hydroperoxide.

7. The process according to claim 4 wherein there is about 0.5 to 10 moles of water per mole of organic hydroperoxide.

8. The process according to claim 7 wherein there is 0.1 to 6 moles of water per mole of organic hydroperoxide.

9. The process according to claim 5 wherein there is about 0.001 to 0.03 mole of catalyst per mole of organic hydroperoxide.

10. The process according to claim 9 wherein there is 0.1 to 6 moles of water per mole of organic hydroperoxide.

11. The process according to claim 10 wherein the metal is molybdenum.

12. The process according to claim 11 wherein the catalyst is molybdenum naphthenate, the organic hydroperoxide is t-butyl hydroperoxide and the olefinically unsaturated hydrocarbon compound is 2-methyl-2-butene.

13. A process for the preparation of methyl isopropyl ketone by the reaction of t-butyl hydroperoxide with 2-methyl-2-butene in the presence of from about 0.001 to 0.03 mole of molybdenum naphthenate per mol of t-butyl hydroperoxide and 0.1 to 6 moles of water per mole of t-butyl hydroperoxide at a temperature in the range of 140° to 250° C.

14. A process for preparing ketones which comprises reacting an olefinically unsaturated hydrocarbon compound having 4 to 30 carbon atoms and a structure selected from the group consisting of where each R is independently a hydrocarbon radical containing from 1 to 14 carbon atoms, $R_1$ is a hydrocarbon radical having 2 to 28 carbons and each $R_2$ is independently a hydrogen or hydrocarbon radical containing 1 to 14 carbon atoms with an organic hydroperoxide having the structural formula $R_3OOH$ wherein $R_3$ is an alkyl, cycloalkyl, aralkyl, alkaryl, aralkenyl, hydroxyaralkyl, cycloalkenyl, or hydroxycycloalkyl hydrocarbon radical having 3 to 20 carbon atoms in the presence of water and a catalytic amount of molybdenum, naphthenate, sterate, octoate or carbonyl.

15. A process for preparing ketones which comprises reacting an olefinically unsaturated hydrocarbon compound having 4 to 30 carbon atoms and a structure selected from the group consisting of

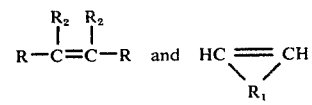

where each R is independently a hydrocarbon radical containing from 1 to 14 carbon atoms, $R_1$ is a hydrocarbon radical having 2 to 28 carbons and each $R_2$ is independently a hydrogen or hydrocarbon radical containing 1 to 14 carbon atoms, with tertiary butyl hydroperoxide, isoamyl hydroperoxide, t-amyl hydroperoxide, methyl ethyl ketone hydroperoxide, cyclohexanone hydroperoxide, methylcyclohexene hydroproxide, cumene hydroperoxide, ethyl benzene hydroperoxide, toluene hydroperoxide, ethyl toluene hydroperoxide, o-xylene hydroperoxide, or phenylcyclohexane hydroperoxide in the presence of water and a catalytic amount of a naphthenate, sterate, octoate or carbonyl of a metal selected from the group consisting of molybdenum, vanadium, tungsten, titanium, niobium, tantalum, rhenium, selenium, chromium, zirconium, tellurium and uranium at a temperature in the range of 140° to 250° C.

16. A process for preparing ketones which comprises reacting an olefinically unsaturated hydrocarbon compound having 4 to 30 carbon atoms and a structure selected from the group consisting of

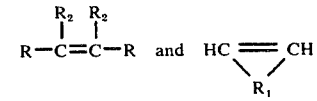

where each R is independently a hydrocarbon radical containing from 1 to 14 carbon atoms, $R_1$ is a hydrocarbon radical having 2 to 28 carbons and each $R_2$ is independently a hydrogen or hydrocarbon radical containing 1 to 14 carbon atoms, with an organic hydroperoxide having the structural formula $R_3OOH$ wherein $R_3$ is an alkyl, cycloalkyl, aralkyl, alkaryl, aralkenyl, hydroxyaralkyl, cycloalkenyl, or hydroxycycloalkyl hydrocarbon radical having 3 to 20 carbon atoms in the presence of water and a catalytic amount of a naphthenate, sterate, octoate or carbonyl of a metal selected from the group consisting of molybdenum, vanadium, tungsten, titanium, niobium, tantalum, rhenium, selenium, chromium, zirconium, tellurium and uranium at a temperature in the range of 140° to 250° C.

* * * * *